US008557863B2

(12) United States Patent
Aylor et al.

(10) Patent No.: US 8,557,863 B2
(45) Date of Patent: Oct. 15, 2013

(54) SUPPRESSION AND PREVENTION OF TUMORS

(76) Inventors: Robert Benson Aylor, Blue Ash, OH (US); Leigh Heather Makover, Ft Myers, FL (US); Robyn Aylor Haines, Columbus, OH (US)

(*) Notice: Subject to any disclaimer, the term of this patent is extended or adjusted under 35 U.S.C. 154(b) by 1655 days.

(21) Appl. No.: 11/526,410

(22) Filed: Sep. 25, 2006

(65) Prior Publication Data

US 2007/0072941 A1  Mar. 29, 2007

Related U.S. Application Data

(60) Provisional application No. 60/720,804, filed on Sep. 27, 2005.

(51) Int. Cl.
*A61K 31/34* (2006.01)
*A61K 31/205* (2006.01)

(52) U.S. Cl.
USPC .......................................... 514/474; 514/554

(58) Field of Classification Search
USPC .................................. 514/474, 554
See application file for complete search history.

(56) References Cited

U.S. PATENT DOCUMENTS

| 5,017,371 | A * | 5/1991 | Cummins | 424/85.6 |
|---|---|---|---|---|
| 6,855,734 | B2 | 2/2005 | Messadek | |
| 2001/0043983 | A1 * | 11/2001 | Hamilton | 426/635 |
| 2002/0192310 | A1 * | 12/2002 | Bland et al. | 424/745 |
| 2003/0077254 | A1 * | 4/2003 | Ramaekers | 424/93.3 |
| 2003/0158166 | A1 * | 8/2003 | Thurlimann | 514/182 |

OTHER PUBLICATIONS

PUBMED.COM, original publication information unknown, one page. Abstract from Exp. Cell. Biol. 1979; 47(6):463-9.
John Francis Freidel, Nonspecific Immunotherapy, with Particular Emphasis on Combined Treatment with Betaine and D-Isoascorbic Acid, as an Antineoplastic Agent, 1979 PHD.
Giuseppe Nacci, The Therapy of Tumors With Gadolium 159 in Nuclear Magnetic Resonance, Chapter 9, May 2000, 4pp.

* cited by examiner

*Primary Examiner* — Shirley V Gembeh

(57) ABSTRACT

Combinations of betaine and vitamin C are used to suppress or prevent malignant tumors, e.g., by combining the two ingredients in an aqueous liquid such as grape juice and the ingredients are usefully provided in containers with instructions for use, especially with support of tests demonstrating the effectiveness of the treatment for, e.g., preventing tumors in populations known to be at risk of developing tumors, and, optionally, treating existing cancers with the combination and other cancer drugs such as anastrozole and/or fulvestrant.

12 Claims, No Drawings

SUPPRESSION AND PREVENTION OF TUMORS

This application claims priority based on Provisional Application No. 60/720,804, filed Sep. 27, 2005, having the same title and inventors.

BACKGROUND OF THE INVENTION

1. Field of the Invention

The invention relates to improvements in minimizing the chances of the occurrence of malignant tumors (cancers) and/or the reduction in the severity of harm from existing malignant tumors, including methods, articles, etc. for providing treatments; and to methods for improving acceptance of such treatments, including methods of improving acceptance of such treatments.

2. Description of Related Art

Beets and citrus fruits have been used historically to treat cancer. Based on this work, a study was carried out by John Francis Freidel as part of his PhD studies at the St. Thomas Institute in 1979 on betaine and D-isoascorbic acid, which are similar to compounds found in beets and citrus fruits, to determine the effect of the combination of these compounds on cancer. The results of the experiments led to the conclusion that "The application of betaine and D-isoascorbic acid as a cancer treatment is not the answer to the cancer problem, but is a new direction along the road to finding a solution to the cancer dilemma." This conclusion was reached despite the fact that the data did indicate that the treatment slowed the progress of cancers.

BRIEF SUMMARY OF THE INVENTION

The combination of betaine (trimethylglycine) and vitamin C (ascorbic acid) or their functional equivalents can be used at effective levels in the treatment of mammals such as humans, canines, felines, etc., either (1) to minimize the risk of cancer, especially in mammals that are either genetically predisposed to cancers, or which are exposed to carcinogens or (2) to treat an existing cancer. The treatment, while not cuing cancer, has been shown to retard the development/progress of cancer. Thus, despite the negative conclusion drawn from previous studies, the treatment can be used either alone or as an adjunct to other chemotherapy treatments; for retarding the progression of an existing cancer until an effective cure or treatment is found; or, most importantly, to use the combination as a prophylactic treatment to keep cancer from developing to the point where it becomes a threat, especially in populations where the risk of developing cancer is greatest, e.g., smokers, people exposed to carcinogenic materials that increase the risk of cancer in the workplace, people having a genetic predisposition to having a particular cancer, animals prone to developing cancer, etc. The combination can be used on mammals, especially humans, dogs, and cats.

B. DETAILS OF THE INVENTION

The invention uses the combination of betaine, or functionally equivalent compounds having similar structures, and vitamin C, or functionally equivalent compounds having similar structures. The betaine and vitamin C can be used at relatively high levels, due to the extensive inherent safety record of these compounds.

Betaine

Betaine, also known as trimethylglycine, is a natural amphoteric compound that is a natural ingredient of many foods such as beets. The structure is the same as acetic acid with one of the hydrogen atoms on the carbon atom attached to the carbonyl carbon being replaced by a trimethyl nitrogen group. Another way of thinking of this type of compound is as a glycine molecule with each of the hydrogen atoms attached to the nitrogen atom being replaced by methyl groups, although other groups, especially other alkyl groups, can also be substituted for the hydrogen atoms. The structure of trimethylglycine is $(CH_3)NCH_2C(O)OH$. The betaine should not be mixed with harmful ingredients. Betaine is mildly basic in water.

The betaine can be in its anhydrous form, its monohydrate form, or in the form of a safe salt, so long as the anion does not cause adverse effects. For treatment of cancer, especially as an adjunct to chemotherapy, injectable forms can be used.

There are many sources for betaine that is pure enough for ingestion, including: Jarrow Formulas™, 1824 S. Robertson Blvd, Los Angeles, Calif. 90035 and Now Foods, 395 S. Glen Ellyn Road, Bloomingdale, Ill. 60108. These products can be found in stores that sell vitamins and other health foods such as GNC™, 300 Sixth Avenue, Pittsburgh, Pa. 15222.

In general, natural sources of betaine, or trimethylglycine, are used to minimize concerns of the individuals taking or using the betaine. Betaine is also available in pharmaceutical quality, since it is an "orphan drug" available as Cystadane™ for the treatment of homocystinuria. The betaine is readily available as the monohydrate, in anhydrous form, as the hydrochloric acid salt, etc. and in capsule, powder, and crystal forms. Very useful betaine forms are the hydrate and anhydrous powder forms since they readily dissolve in aqueous liquids. The commonly available salt is the hydrochloric acid salt that is used to help people with insufficient hydrochloric acid in their stomach digest proteins. It is desirable to avoid the use of this salt if one already has sufficient acid in the stomach and it is desirable to take the salt with protein in the stomach.

Betaine is a nutrient that plays an important role in the health of the cardiovascular system. Studies have suggested that betaine, along with other nutrients, helps to reduce potentially toxic levels of homocysteine (Hcy), a naturally occurring amino acid that can be harmful to blood vessels thereby contributing to the development of heart disease, stroke, and peripheral vascular disease (reduced blood flow to the legs and feet). Accordingly, the taking of relatively high levels of betaine confers additional benefits for health besides inhibiting the development of cancer.

As discussed hereinafter, the desirable benefits from taking betaine provide additional reasons for taking the betaine and vitamin C for prophylactic purposes to minimize the risk of cancer.

Vitamin C

Vitamin C and its normal functional equivalents such as D-isoascorbic acid are readily available. However, the natural vitamin C is a highly desirable version. Vitamin C is available in capsule, caplet, tablet, and powder/crystal forms. Vitamin C also can be dissolved fairly readily in aqueous liquids like water, fruit juices and similar liquids and, is also available in "time release" form. Powdered or crystalline vitamin C in finely divided form is useful for mixing with finely divided betaine. Since the betaine is inherently basic in water, they can help to neutralize each other since the ascorbic acid is acidic in water.

Vitamin C can also be taken at relatively high levels. However, there are possible adverse side effects for high levels. In each instance, the risk of side effects has to be balanced against the risks of the cancer. Where an existing cancer is life threatening, the risk, e.g., of formation of kidney stones should not stop using higher levels, especially for shorter periods of time.

For prophylactic purposes, the level of vitamin C can be less, typically less than about three grams per day.

Additional Benefits

While the main benefit of a person or pet taking vitamin C and betaine in combination is the prevention/suppression of tumors, as mentioned before, additional benefits can be obtained depending upon the levels taken. Betaine improves cardiovascular health, and can benefit people with fatty deposits in the liver. Also, after only a few doses of the betaine at a level of about one and a half to about three grams per day, the tendency of people, especially older people, to be "light headed" when they get up after prolonged squatting or kneeling is considerably lessened. After only a few weeks of taking the betaine, cholesterol levels are reduced and the ability to lose weight is improved.

These benefits are related to the ability of betaine to enhance the mobility of fatty substances like cholesterol, thus promoting their digestion and/or removal of unwanted fatty deposits. Recently there has been considerable discussion of possible liver side effects attributed to cholesterol lowering drugs like Lipitor™ (atorvastatin calcium) and Zocor™ (simvastatin), which are hydroxymethylglutaryl coenzyme A reductase inhibitors (statins). Thus, the ability of betaine to assist in lowering cholesterol levels is desirable. Combinations of betaine and Lipitor and other cholesterol lowering drugs provide additional cholesterol lowering since the mode of action is different, allowing for the use of lower levels of the stains.

The heart problems alleged to be the result of taking pain medications like Vioxx™ can be the result of the reduced stomach problems caused by the use of Vioxx as compared to traditional pain relievers like aspirin. Less stomach problems undoubtedly leads to a greater tendency to overeat, leading to weight gain, which results in higher risk of heart attacks. The use of betaine reduces this risk.

Treating people diagnosed with high cholesterol with high dosages of betaine; combining betaine and other cholesterol lowering compounds for improved performance; and treating pain with pain medications like Vioxx and betaine to decrease the tendency of the patient to gain weight, can decrease the risk of adverse heart effects from taking such medications.

Dosage

For simplification, it can be desirable to provide the betaine and/or vitamin C in single dosage form. The form can be tablet, pill, lozenge, capsule, etc., or powders or crystals in packages, especially packages that provide protection from moisture. Betaine is very hygroscopic. Typically, betaine is packaged in moisture proof containers and optionally with materials to scavenge moisture. When the materials are in a package, it can be desirable to have the package be a water-soluble packet.

It can be desirable to mix the betaine and/or the vitamin C in finely divided forms with water, fruit juice, or similar beverages where they quickly dissolve. The amounts taken are dependent on the weight of the mammal being treated and finely divided forms allow for adjusting the dosage for different body weights and to adjust for adverse effects.

It is believed that n immediately before taking the liquid is advantageous. The instructions for betaine in its pharmaceutical form state that the product should be taken immediately after mixing with water. It is believed that part of the actives can react and form more insoluble materials that are less bioavailable. Addition of a suspending agent can provide longer waiting time while maintaining efficacy.

In general, the effective doses for each ingredient can be determined readily by creating a dose response curve using one or more animal models and testing against similar cancers. The adverse effects of taking these levels of betaine and vitamin C are not believed to create a sufficient risk to make the risk/benefit ratio too high for normal use. Vitamin C, e.g., can cause kidney stones and diarrhea at higher levels, so the dosage should be started at a safe level, about 1 gram per day or less, and the level should then be raised slowly. Some people can take vitamin C at levels of up to 25 grams per day, but, in general, doses of vitamin C are usually about 3 grams per day or less.

Similarly, although betaine has no known serious side effects, the level can be initially about 1 gram per day or less and the level can be raised slowly. The use of high levels of these ingredients is usually not recommended in young children, pregnant women, etc. However, if cancer is present, the risk/benefit ratio becomes lower because of the extreme risk from the cancer. For safety, unless the cancer risk is great, the amount taken should be less than the amount that causes uncomfortable side effects, so starting at a low level and increasing the dosage until side effects are noticed is an acceptable approach.

For prophylactic purposes, the combination of several animal experiments is a good approach before the dosage is selected for maximum prevention while avoiding any serious side effects. Typical dosage levels for normal size adults are about one gram per day, or more or less, of each ingredient, betaine and vitamin C, when cancer is not present to inhibit formation of cancerous growths (tumors) and about three grams per day, or more or less, when cancer has been diagnosed. For prevention, the level will usually be at least at the one gram per day level, although the dosage of betaine can usefully be at least at the gram and a half a day level for other reasons related to cardiovascular health and the level of vitamin C is related, at least in part to its value at gram per day levels and above for avoidance/treating of infections such as colds, etc.

Levels of vitamin C and/or betaine from about one half gram to about 25 grams each per day can be used depending upon the individual's ability to tolerate the dose and the severity of the cancer. A realistic dose response curve can be generated using a variety of species normalized for the weight of the combination and/or its components per weight of the species.

Higher levels can be used where the cancer is life threatening, since the adverse effects of both betaine and vitamin C are relatively low and relatively minor. For treatment of an existing cancer, the highest level that can be tolerated is typically used. Levels of about 20 mg./kg. of betaine and an equivalent level of vitamin C, taken twice daily (total of about 40 mg./kg.) give good results. Daily prophylactic doses, in increasingly desirable levels, are at least 1 mg./kg., 5 mg./kg., 10 mg./kg., 20 mg./kg., for each of the compounds and the maximum levels are less than about 100 mg./kg., 80 mg./kg., 60 mg./kg., and 40 mg./kg. Typically the doses are divided into at least two separate doses to provide less material in each dose and to spread the effect. From about 5 mg./kg. to about 40 mg./kg. per day, or from about 10 mg./kg. to about 30 mg./kg. per day are typical prophylactic doses, but higher levels are better if the higher levels can be tolerated without adverse effects.

Adverse effects for betaine are not normally observed at most reasonable levels and people who take it for its approved pharmaceutical usage typically take at least about six grams a day. Vitamin C can cause some stomach problems at levels above about three grams a day, but usually more can be taken without adverse effects. The risk of minor adverse effects is sufficient to minimize dosages for prophylactic use, but should not be determinative when there is an existing cancer, especially in life threatening form.

The combination of betaine and vitamin C can be taken, or given, in an effective amount with a high degree of safety to prevent cancer or until an existing cancer is "cured", or a complete cure for the cancer is found. When the patient already has cancer, the combination can be taken either alone, or as a supplement to a prescribed treatment, although there has been some information that free radical scavengers like vitamin C may decrease the benefit of ionizing radiation like X-rays. Although this data seems to be based upon short studies, if the treatment comprises radiation, the oncologist may not want to use vitamin C. The use or non-use of the combination by the oncologist or other medical personnel will depend upon their preference.

Due to the safety of the ingredients, longer treatments are possible when the patients survive treatment with anticancer drugs to maintain health and minimize recurrence of the cancer. Typically, since the present treatment has not been found to destroy the cancer, treatments will continue for years. Prophylactic uses will necessarily involve long times, on the order of at least years.

Treatment Compositions

A very convenient way to prepare the combination is to add anhydrous or hydrated betaine powder and vitamin C powder or crystals to water, or, desirably, a fruit drink or other flavored drink, to create a single dose and then promptly taking the dose to avoid any possibility of creating an insoluble reaction product. The reaction product of the betaine and vitamin C in aqueous solution, e.g., trimethylglycine ascorbate, is also valuable and can be used.

The version involving dissolving the two ingredients in grape juice has been used effectively and is believed to be desirable since the apparent active ingredient is presented in very finely divided form, which increases bioavailability. The use of separate powders or capsules delays the absorption of the ingredients. In any dose/response study, the effect of separate and combined powder dosing, separate capsule dosing, and especially separate or combined ingredients in a time release format are studied to provide an indication of the more effective presentations.

The ingredients can also be dissolved in water or other liquid such as a fruit juice and absorbed, either individually or together, onto a solid material suitable for ingestion. For animals, the betaine and vitamin C are desirably added to the food or water, but in order to make sure the proper dose is taken, a desirable way will be to include the ingredients in a treat that conceals the active ingredients and which therefore is more likely to be taken and consumed immediately. Therefore, a very desirable product is a food, especially a treat, with the betaine and vitamin C already in the food or treat. It has been found that the betaine and vitamin C can be dissolved in water and absorbed on solids such as Cheerios™. If the vitamin C is present in sufficient amount to provide an acidic effect, the resulting "citric" taste can be modified by use of a sweetener. Since the betaine tends to be hygroscopic, it is desirable to package any such food to prevent absorption of water. For a given level of ingredients, it can be desirable to package the food in individual packages of the correct dosage to avoid under/over treatment.

For animals, a food with the ingredients at the right levels is desirable to ensure the treatment is taken. For dogs, concealment of the actives in peanut butter is effective and in cats, concealment in a liver paste is effective. For dogs, tablets or finely divided forms can be encapsulated and for cats, the powders can be encapsulated and used. Any form that results in the animal willingly ingesting the actives is acceptable. Experience has shown, however, that use of several different food products to conceal the active is highly desirable, since pets tend to change their tastes and/or discover that the specific product conceals the dosage. For convenience, it is desirable to add the betaine and/or the vitamin C to an existing food and add a material to disguise and/or obscure the taste and/or feel of the betaine and vitamin C. For dogs, the level of vitamin C can be lowered due to the fact that dogs manufacture vitamin C. However, it is better to err on the side of too much rather than too little.

For dogs, the encapsulation of the ingredients in food, or desirably a snack, is acceptable since dogs tend to eat their food without first chewing it. For felines, it is desirable to make a paste of meat or fish and incorporate the ingredients, especially the vitamin C. In extreme cases, the ingredients can be put down the throats of the animals in some more concentrated form like tablets or capsules.

For humans, the use of food or drink to provide a dose of the combination is not essential, but can be used to increase the compliance with the treatment regimen. For humans, grape juice, diet colas such as Coca Cola™, apple juice, coffee, and water are effective to make the dosage more palatable. Water does not conceal the taste of the ingredients and while they are not impossible to take in water, they are much better tolerated in other drinks. The ingredients in capsule or tablet form will normally be coated with an ingredient that minimizes the taste. However, the use of liquid versions is more effective and the use of finely divided actives added to liquids allows for adjustment of the levels for weight and/or avoiding adverse effects.

One of the observations of additional benefits, is that the vitamin C provides a fresh citrus note to drinks like diet colas, apple juice, tea, etc., that is highly desirable. The use of high levels of vitamin C in such drinks is not desirable without warnings about the danger of taking too much vitamin C and instructions to provide guidelines for usage provided by instructions in association with the products. However, lower levels of vitamin C in such drinks is a highly desirable way of adding vitamin C to the diet and when combined with betaine, are an effective way to provide the treatment.

The use of aqueous liquids in which the betaine and vitamin C are added in finely divided form and then immediately ingested is desirable. It is important to use ingredients and methods of dosing that do not affect bioavailability.

In general, injection is avoided to limit the risk of infection, but it is known that injection is the most effective way to increase bioavailability. Injection, however, typically is done by tried professionals, thus increasing the cost of an operation that will be repeated for the rest of the animal's life, since the combination will normally not totally eradicate the cancer. Injection can be used effectively in chemotherapy, where trained medical personnel are available, but again, the treatment is used for a long time, so a treatment method that does not require trained personnel is desirable.

Food and Food Supplements

The amount of each ingredient added to a food or food supplement is determined by the total amount that can be tolerated and the amount of the food or food supplement that is taken. An example of this approach is U.S. Pat. No. 6,866,862, Huber, et al., Mar. 15, 2005 for "Animal feeds including heartworm-prevention drugs". The food containing the treatment is especially useful for treating animals such as dogs, cats, horses, cows, etc. For animals, one can mix the betaine and vitamin C in an aqueous liquid, apply the liquid to dry animal food, desirably immediately, and then dry the food and package it, desirably in packaging that prevents absorption of water.

Method of Providing Products

The materials used in the treatments herein are readily available. Therefore, it is essential that the materials used in the treatment methods herein should be sold with instructions for the proper method of treatment. The treatment methods disclosed herein should be backed by at least one controlled study demonstrating the value of the method, especially a study that is controlled for the species and specific risk and the actives and/or products for practicing the treatment methods are desirably provided in association with instructions for usage, dosage, preparation of products, cautions of possible adverse effects, etc. "In association with" as used herein comprises any communication that provides the needed information, including advertisements, printing on packages or print products packed with the materials or infomercials, cartoons, etc. The important thing is that people know that the dosages and continuous treatment are important to providing the desired benefits.

Desirably, the treatment methods should be approved by at least one governmental agency that will provide the desired confidence that the method will provide the desired result. This is especially important for the preventative (prophylactic) use of the method. Failure to continue the treatment can be very harmful. The preferred studies for the preventative treatment are controlled studies in the specific species and for the specific cancer. E.g., for humans, a controlled study in smokers who are subject to developing lung cancer, young women who are subject to developing breast cancer, people with genetic predisposition to a type of cancer such as colon or uterine cancers, etc., should each be a separate study to provide the most meaningful input guaranteeing that the individuals in the target group will understand the value of the treatment and thus continue the treatment. A useful method for providing confidence of the result is to test the combination on an animal model where the animal is exposed to an ingredient known to cause cancer to show that the treatment does in fact provide protection.

Specific Treatment

One specific treatment comprising the combination of betaine and vitamin C is the treatment of breast cancer, especially breast cancer that reappears after an initial treatment that has resulted in years where the cancer was not detected. The combination has been shown to be effective, especially in combination with cancer treating drugs like Faslodex™ (fulvestrant) and/or Arimidex™ (anastrozole). The combination of Faslodex, Arimidex, betaine, and vitamin C has been shown to be an effective suppressant for breast cancer that has returned after years of freedom from cancer.

Faslodex is typically given as an injection intramuscularly once a month (250 mg. in 5 ml.). Arimidex is typically given as a 1 mg. pill once a day. The betaine and vitamin C are taken as powders dissolved in, e.g., a fruit juice such as grape juice, typically twice a day at a level of about 20 mg./kg. of each powder, which for an approximately 150 pound adult is about one and a half grams of each compound taken twice daily.

There has been considerable comment about the possibility of high dosages of vitamins, especially vitamin C interfering with cancer treatments such as radiation. Furthermore, most comments in recent history have warned against adding any additives or supplements to any cancer treatment. Thus, the current teachings of experts in the field of oncology are consistently to avoid practicing the present invention. However, in each instance, only a controlled study can answer the question of whether supplements can provide a benefit. The conditions of the study should be selected to correctly predict the outcome. The method of providing the proper materials with the proper information for effecting the treatment described herein can offset the negative statements that have been made by providing specific positive indications.

Another specific treatment is to provide prophylactic doses to smokers. Additionally, a recent study indicates that oral products, like chewing tobacco and snuff, can be used by smokers to lower the risk of cancer and incidentally the risk of damage to lungs by the smoke. However, there is still a risk of developing cancer. Use of the treatment herein and even inclusion of betaine and vitamin C in such products reduces this remaining risk.

EXAMPLES

Example 1

A German shorthaired pointer dog was diagnosed by a veterinarian as having a cancer. For about ten years, the dog, weighing about 80 pounds, was given about one gram of betaine and about one gram of vitamin C in the form of tablets concealed in peanut butter, bread, meat treats, etc., and, after the first diagnosis, and several months of treatment, there was no evidence of an active cancer in subsequent visits to veterinarians. Since there was no evidence of cancer, the treatment was eventually stopped after several years. About three months after the suspension of the treatment, the dog died, apparently according to the veterinarian, of lung cancer.

Example 2

Based upon information received from a veterinarian, a cat with cancer was treated with betaine and vitamin C and after the cancer was believed to be controlled, the cat was returned to the owner. However, the treatment was not continued and the cancer returned.

Example 3

A woman who had breast cancer and, who after treatment by removal of the breast followed by radiation and chemotherapy was free of detectable cancer for a period of about 15 years, redeveloped cancer. At that time, the cancer reappeared as a tumor on a bone in the shoulder, causing great pain. The woman was told that the previous treatments had been so exhaustive, that they left her no treatment but a hormone therapy that would merely slow the tumor's progression. The woman began the hormone therapy and added three grams of betaine and three grams of vitamin C as powders dissolved in grape juice, with the dosage being split into two equal amounts, morning and evening. After one year, the markers indicating the presence of the cancer were in the low normal range and the tumor was shrinking. The treatment continues and the patient intends to continue the treatment indefinitely.

Example 4

Approximately one and a half grams of betaine monohydrate powder and one and a half grams of crystalline vitamin C are dissolved in water and added to sufficient Cheerios to absorb the mixture. The taste of the Cheerios is acceptable, but with a distinct acidic citrus flavor. Addition of Splenda™ to the Cheerios, made the taste very acceptable and provided a citrus "treat" that would be easy to incorporate into a daily routine. Each helping is a dose.

Example 4

One and a half grams each of betaine monohydrate powder and vitamin C crystals are mixed into a full glass of either apple juice, Diet Coca Cola, coffee, and water. The tastes of the apple juice, Coca Cola, and coffee were found to be more acceptable that the water mixture and each glass of liquid is an acceptable dosage, either taken once or twice a day.

Each of these food products and drink products are desirable for providing the treatments described herein.

Example 5

Laboratory animals susceptible to the formation of tumors ingest amounts based on fixed ratios of mixture of betaine and vitamin C, to their body weights, (5, 10, 20, 30, or 40 mg./kg.) either before, or after inducing the formation of a cancerous tumor to determine effective amounts of the mixture for preventing, or minimizing the progress of, cancerous tumors. Suitable animals can be obtained from commercial sources such as The Jackson Laboratory, 600 Main Street, Bar Harbor, Me. 04609 (mice) and Corance Research Products, Inc., Denver, Pa. (Outbread New Zealand White rabbits). There are other models such as those disclosed in an article by J. L. Brodsma, Z. Yang, and E. A. Johnson in Proceedings of the National Academy of Sciences of the United States of America, Vol. 88, 4816-4820, in which cottontail rabbits are inoculated to induce the formation of pappilomas. The results are then used to set acceptable dosage requirements for treatments to prevent or suppress the development of cancer tumors. These amounts are then desirably refined by clinical tests in the population that is to be treated to confirm the dosage effectiveness.

What is claimed is:

1. A method of treatment which minimizes the risks associated with a cancer tumor either by minimizing the chances of formation of a cancer tumor, or by suppressing the development of any existing cancer tumor, comprising treating a human, a canine, or a feline, including humans, canines, and felines known to either have a cancer tumor or who have had an exposure to a carcinogen or who have a genetic disposition to form cancer tumors, said method of treatment comprising administering, either separately or together, effective amounts of betaine or its functional equivalent, and vitamin C or its functional equivalent, said effective amounts of each of the betaine and vitamin C being at least about 5 mg per kg per day of the weight of the human, canine, or feline, until there is no more risk of damage from the cancer tumor said method specifically comprising treating breast cancer in humans with an effective amount of betaine and vitamin C, and where the treatment optionally also comprises an additional hormonal anticancer agent which optionally is either anastrozole, fulvestrant, or combinations of anastrozole and fulvestrant.

2. A method of treatment which minimizes the risks associated with a cancer tumor either by minimizing the chances of formation of a cancer tumor, or by suppressing the development of any existing cancer tumor, comprising treating a human, a canine, or a feline, including humans, canines, and felines known to either have a cancer tumor or who have had an exposure to a carcinogen or who have a genetic disposition to form cancer tumors, said method of treatment comprising administering, either separately or together, effective amounts of betaine or its functional equivalent, and vitamin C or its functional equivalent, said effective amounts of each of the betaine and vitamin C being at least about 5 mg per kg per day of the weight of the human, canine, or feline, until there is no more risk of damage from the cancer tumor wherein the method is specifically for treating canines or felines where the betaine and vitamin C are mixed in a dry food product which is then used to feed the animal, and where the treatment is supported by at least one controlled study, said study optionally being approved by one or more recognized authorities, and optionally being in an animal model where the animal is exposed to a condition known to create tumors.

3. The method of claim 2 where canines are treated.

4. The method of claim 2 wherein the cancer is lung cancer.

5. A method of treatment which minimizes the risks associated with a cancer tumor either by minimizing the chances of formation of a cancer tumor, or by suppressing the development of any existing cancer tumor, comprising treating a human, a canine, or a feline, including humans, canines, and felines known to either have a cancer tumor or who have had an exposure to a carcinogen or who have a genetic disposition to form cancer tumors, said method of treatment comprising administering, either separately or together, effective amounts of betaine or its functional equivalent, and vitamin C or its functional equivalent, said effective amounts of each of the betaine and vitamin C being at least about 5 mg per kg per day of the weight of the human, canine, or feline, until there is no more risk of damage from the cancer tumor wherein specifically humans are treated and the amount of each of betaine and Vitamin C taken per day is at least 1000 mg.

6. The method of claim 5 wherein the cancer is colon cancer.

7. The method of claim 5 wherein the cancer is lung cancer.

8. The method of claim 5 wherein the cancer is uterine cancer.

9. The method of claim 5 wherein the cancer is breast cancer.

10. A method of treatment which minimizes the risks associated with a cancer tumor either by minimizing the chances of formation of a cancer tumor, or by suppressing the development of any existing cancer tumor, comprising treating a human, a canine, or a feline, including humans, canines, and felines known to either have a cancer tumor or who have had an exposure to a carcinogen or who have a genetic disposition to form cancer tumors, said method of treatment comprising administering, either separately or together, effective amounts of betaine or its functional equivalent, and vitamin C or its functional equivalent, said effective amounts of each of the betaine and vitamin C being at least about 5 mg per kg per day of the weight of the human, canine, or feline, until there is no more risk of damage from the cancer tumor wherein humans are treated and comprising minimizing the risk of the occurrence of a cancer tumor in a mammal by treating said mammal with an effective prophylactic amount, optionally on a daily basis, with a combination of betaine or its functional equivalent and vitamin C or its functional equivalent, which optionally can be further combined with one or more ingredients to disguise or hide the taste of the betaine and vitamin C, and which optionally can be mixed together in an aqueous liquid comprising said ingredients immediately before consumption and wherein the betaine and vitamin C are combined with an additive to conceal or disguise the taste of the betaine and/or vitamin C to maximize the acceptance of the treatment and said additive can optionally be an aqueous liquid, which is optionally a fruit or vegetable juice, and where the betaine and vitamin C can optionally be added to the aqueous liquid immediately prior to ingestion of the aqueous liquid and wherein and the amount of each of betaine and Vitamin C taken per day is at least 1000 mg.

11. A method of treatment which minimizes the risks associated with a cancer tumor either by minimizing the chances of formation of a cancer tumor, or by suppressing the development of any existing cancer tumor, comprising treating a human, a canine, or a feline, including humans, canines, and felines known to either have a cancer tumor or who have had an exposure to a carcinogen or who have a genetic disposition to form cancer tumors, said method of treatment comprising administering, either separately or together, effective amounts of betaine or its functional equivalent, and vitamin C or its functional equivalent, said effective amounts of each of the betaine and vitamin C being at least about 5 mg per kg per day of the weight of the human, canine, or feline, until there is no more risk of damage from the cancer tumor and wherein the betaine and vitamin C are combined with an additive to conceal or disguise the taste of the betaine and/or vitamin C to maximize the acceptance of the treatment and said additive can optionally be an aqueous liquid, which is optionally a fruit or vegetable juice, and where the betaine and vitamin C can optionally be added to the aqueous liquid immediately prior to ingestion of the aqueous liquid and specifically wherein humans are treated and wherein and the amount of each of betaine and Vitamin C taken per day is at least 1000 mg.

12. A method of treatment which minimizes the risks associated with a cancer tumor either by minimizing the chances of formation of a cancer tumor, or by suppressing the development of any existing cancer tumor, comprising treating a human, a canine, or a feline, including humans, canines, and felines known to either have a cancer tumor or who have had an exposure to a carcinogen or who have a genetic disposition to form cancer tumors, said method of treatment comprising administering, either separately or together, effective amounts of betaine or its functional equivalent, and vitamin C or its functional equivalent, said effective amounts of each of the betaine and vitamin C being at least about 5 mg per kg per day of the weight of the human, canine, or feline, until there is no more risk of damage from the cancer tumor wherein humans are treated and comprising minimizing the risk of the occurrence of a cancer tumor in a mammal by treating said mammal with an effective prophylactic amount, optionally on a daily basis, with a combination of betaine or its functional equivalent and vitamin C or its functional equivalent, which optionally can be further combined with one or more ingredients to disguise or hide the taste of the betaine and vitamin C, and which optionally can be mixed together in an aqueous liquid comprising said ingredients immediately before consumption and wherein the betaine and vitamin C are combined with an additive to conceal or disguise the taste of the betaine and/or vitamin C to maximize the acceptance of the treatment and said additive can optionally be an aqueous liquid, which is optionally a fruit or vegetable juice, and where the betaine and vitamin C can optionally be added to the aqueous liquid immediately prior to ingestion of the aqueous liquid and specifically treating humans wherein and the amount of each of betaine and Vitamin C taken per day is at least 1000 mg.

* * * * *